United States Patent [19]
Kawaguchi et al.
[11] Patent Number: 4,533,631
[45] Date of Patent: Aug. 6, 1985

[54] FERMENTATION PROCESS FOR PREPARATION OF ANTIBIOTIC BU-2517

[75] Inventors: Hiroshi Kawaguchi, Tokyo; Masataka Konishi, Yokohama; Koko Sugawara, Wako; Koji Tomita, Kawasaki, all of Japan

[73] Assignee: Bristol-Myers Company, New York, N.Y.

[21] Appl. No.: 478,751

[22] Filed: Mar. 25, 1983

Related U.S. Application Data

[62] Division of Ser. No. 339,355, Jan. 15, 1982, Pat. No. 4,409,210.

[51] Int. Cl.$^3$ ........................ C12P 21/02; C12N 1/20
[52] U.S. Cl. ........................................ 435/70; 435/253
[58] Field of Search .................... 435/68, 70, 243, 253; 424/177; 260/112.5 R

[56] References Cited

U.S. PATENT DOCUMENTS 3,061,516 10/1962 Hooper et al. ...................... 424/119
3,126,317 3/1964 Heineman et al. .................. 424/118

FOREIGN PATENT DOCUMENTS 3130601 4/1977 Japan .

OTHER PUBLICATIONS

Heineman, B. et al., Amphomycin, A New Antibiotic, Dec. 1953, Antibiotics and Chemotherapy.
Bodansky, M. et al., Structure of the Peptide Antibiotic Amphomycin, Apr. 4, 1973, J. Am. Chem. Soc., pp. 2352–2357.
Takahara, Y. et al., Isolation of a New Peptide Antibiotic . . . J. of Antibiotics, Feb. 1979, pp. 115–120.
Takeuchi, Y. et al., The Structure of Permetin A . . . in J. of Antibiotics, Feb. 1979, pp. 121–129.
Kupak, J. et al., Antibiotics from Basidiomycetes . . . J of Antibiotics, Feb. 1979, pp. 130–135.
Misiek, M. et al., Telomycin, A New Antibiotic Antibiotics Annual 1957–1958, pp. 852–855.

*Primary Examiner*—Thomas G. Wiseman
*Assistant Examiner*—Jean A. Heck
*Attorney, Agent, or Firm*—David M. Morse

[57] ABSTRACT

Disclosed is a process for preparation of the water-soluble peptide antibiotic designated Bu-2517 by fermentation of Empedobacter sp. strain G393-B445 (ATCC 31962).

4 Claims, No Drawings

FERMENTATION PROCESS FOR PREPARATION OF ANTIBIOTIC BU-2517

This application is a division of our copending application Ser. No. 339,355 filed Jan. 15, 1982, now U.S. Pat. No. 4,409,210.

BACKGROUND OF THE INVENTION 1. Field of the Invention

This invention relates to a new water-soluble peptide antibiotic, to methods for its production and isolation, to pharmaceutical compositions containing it and to methods of using said antibiotic as an antimicrobial agent.

2. Description of the Prior Art

The new antibiotic of the present invention is a water-soluble cyclic acyl octapeptide containing D-proline, D-serine, L-proline, L-arginine, D-threo-β-hydroxyaspartic acid, D-serine, L-trans-3-hydroxyproline and L-threo-β-hydroxyaspartic acid and a $C_{14}$ fatty acid residue of 3-hydroxytetradecanoic acid. The new antibiotic is produced by fermentation of Empedobacter sp. strain G393-B445 (ATCC 31962).

A literature search carried out on behalf of the present applicants has failed to uncover any polypeptide antibiotics containing the same constitutive amino acids and fatty acid residue as the antibiotic of the present invention (designated by the inventors as Bu-2517). Among the polypeptide antibiotic reported in the literature, however, Bu-2517 has some similarities to amphomycin (*Antibiot. Chemother.* 3: 1239–1242, 1953; *J. Am. Chem. Soc.* 95:2352, 1973, U.S. Pat. No. 3,126,317) in its amphoteric nature, to antibiotic BA-843 (Japan Kokai 130,601/53; Farmdoc 92052A/51) in the producing organism and some of the constitutive amino acids and to permetin A (*J. Antibiotics* 32:115–120, 1979; *J. Antibiotics* 32:121–135, 1979) in the cyclic depsipeptide structure. An amino acid component of Bu-2517, trans-L-3-hydroxyproline, is one of the structural constituents of telomycin (*Antibiotics Ann.* 1957/1958, 852–855; U.S. Pat. No. 3,016,516). All of the polypeptide antibiotics mentioned above, however, may be clearly differentiated from Bu-2517 in their chemical and biological properties.

SUMMARY OF THE INVENTION

There is provided by the present invention a new water-soluble peptide antibiotic designated Bu-2517, said antibiotic being produced by cultivating a new strain of Empedobacter designated Empedobacter sp. strain G393-B445 (ATCC 31962), or variants or mutants thereof, in an aqueous nutrient medium containing assimilable sources of carbon and nitrogen under submerged aerobic conditions until a substantial amount of Bu-2517 antibiotic is produced by said organism in said culture medium and, subsequently, recovering the Bu-2517 antibiotic from the culture medium. Bu-2517 is an amphoteric compound and may be obtained either in the zwitterionic form or as a pharmaceutically acceptable acid- or base-addition salt.

DETAILED DESCRIPTION

This invention relates to a new water-soluble peptide antibiotic designated herein as Bu-2517 and to its preparation by fermentation of a new strain of Empedobacter designated Empedobacter sp. strain G393-B445. The producing organism is an unusual bacterial strain which was isolated from a soil sample collected in the Yamate-Dori, Tokyo, by means of a modified pollen bait technique [see *J. Elisha Mitchell Sci. Soc.* 79:53–70 (1963)]. The organism attached to and grew on a grain of pine pollen floating on the surface of a soil-water suspension. A culture of this organism has been deposited in the American Type Culture Collection, Washington, D.C., and added to its permanent collection of microorganism as ATCC 31962.

TAXONOMY OF THE PRODUCING ORGANISM

Strain G393-G445 is a gram-negative, asporogenic rod bacterium. The cells vary in shape from coccobacilli to slender rods and are motile with peritrichous flagella. The morphology of strain G393-B445 is summarized below in Table 1.

TABLE 1

Morphology of strain G393-B445

| | |
|---|---|
| Shape of cells | Coccobacilli to slender rods. Occasional occurrences of partially swollen or curved filaments and vacuolated cells. Rounded ends. Occuring singly or in pair. |
| Size of cells, μm | 0.5~0.8 × 1.0~3.0. Some, 5~10 in length |
| Spore | Not formed |
| Motility | Motile with peritrichous flagella. Concominant formation of non-flagellated non-motile cells. |
| Number of flagella in a cell | 4~10 |
| Fimbriae | Scarcely borne |
| Gliding movement of single cells or cell mass | None |
| Gram-stain | Negative |

Strain G393-B445 gives vigorous growth on nutrient agar and YP medium (yeast extract 0.03%, peptone 0.1%, NaCl 0.01%, pH 6.6-6.8) and produces two types of colonies, R (rough) and S (smooth) forms. It is mesophilic, oxidative, alkali-sensitive and halophobic. The cultural and physiological characteristics of strain G393-B445 are shown in Table 2 below.

TABLE 2

Cultural or Physiological Characterization of Strain G393-B445

| Colony on nutrient agar | | | | Occurrence of two forms of colonies, R and S | | | |
|---|---|---|---|---|---|---|---|
| | Form | Surface | Edge | Elevation | Optical property | Color | Swarming |
| R | Irregular or wrinkled | Rough | Undulate | Raised and effuse | Translucent | Pale-yellow | Negative |
| S | Circular | Smooth | Entire | Raised | Translucent | Pale-Yellow | Negative |
| Growth on nutrient broth | | | | Formation of pellicle. Slight turbidity. Flocculent sediment. | | | |
| Cellular carotinoid pigment | | | | not detected (spectrophotometry) | | | |
| Growth temperature* | | | | Growth 7° C. to 42° C. | | | |
| | | | | No growth 0° C. and 45° C. | | | |
| NaCl tolerance* | | | | Growth 1.0% NaCl or less | | | |

TABLE 2-continued

| Cultural or Physiological Characterization of Strain G393-B445 | | | | |
|---|---|---|---|---|
| | No growth | 2.0% NaCl or more | | |
| NaCl requirement* | — | | | |
| pH tolerance* | Growth | pH 5.0 to 7.5 | | |
| | No growth | pH 4.5 or less, and pH 8.0 or more | | |
| Heating at 70° C. for 10 min* | Not survived | | | |
| Growth on | Anaerobic agar | | | − |
| | Glucose-ammonium salts agar | | | + |
| | Bile-aesculin agar | | | − |
| | MacConkey agar | | | + |
| | NAC agar (Nalidixic acid-cetrimide agar) | | | − |
| Hydrolysis of | Gelatin | + | Chitin | + |
| | Casein | − | Alginate | − |
| | Starch | + | Tween 20 | + |
| | Agar | − | Tween 80 | + |
| | Cellulose | − | | |
| | CM-cellulose | − | | |
| Oxidative acid production from | Glucose | + | | |
| | Lactose | − | | |
| | Sucrose | + | | |
| | Maltose | + | | |
| Reactions | Methyl red | | | − |
| | Voges-Proscauer | | | − |
| | Citrate alkalization (Simmons) | | | + |
| | Indole | | | − |
| | Pyocyanin-pyorubin (King's A Medium) | | | − |
| | Fluorescens (King's B Medium | | | − |
| | Hydrogen sulfide | | | + |
| | Gas from glucose | | | − |
| | Gas from nitrate and nitrite | | | − |
| | Nitrite from nitrate | | | + |
| | Milk coagulation | | | − |
| | Milk peptonization | | | + |
| | Catalase | | | + |
| | Indophenol oxidase | | | very weak |
| | Urease | | | + |
| | Phenylalanine deaminase | | | − |
| | Phosphatase | | | + |
| | Deoxyribonuclease | | | − |
| | Hemolysis, rabbit blood | | | very weak |

*YP medium was used.

The content of guanine and cytosine (GC content) of cellular DNA analyzed by the method of Bendich (*Methods in Enzymology*, Vol. III, pp. 715–723, Ed. S. P. Colowich and N. O. Kaplan, Academic Press, New York, 1957) was 66.5±1.5 mol%. The antibiotic sensitivity of strain G393-B445 was determined by the paper disc-agar diffusion method. The results are shown in Table 3.

TABLE 3

Sensitivity of Strain G393-B445 to Antibacterial Agents (paper-disc method)

| | | Sensitivity** | | |
|---|---|---|---|---|
| Antibiotics* | amount/disc | Strain G393-B445 | *E. coli* NIHJ | *S. aureus* 209P |
| Actinomycin D | 10 mcg | I | R | S |
| Ampicillin | 10 mcg | S | S | S |
| Chloramphenicol | 30 mcg | S | S | S |
| Erythromycin | 15 mcg | S | R | S |
| Penicillin G | 10 units | S | I | S |
| Polymyxin B | 300 units | R | R | R |
| Streptomycin | 10 mcg | S | I | I |
| Tetracycline | 30 mcg | S | S | S |

*Difco's antibiotic sensitivity discs
**Determined on nutrient agar after 2 day's incubation at 28° C.
Abbreviations: S (sensitive), R (resistant), I (intermediate).

According to the descriptions in *Bergey's Manual* (1974), strain G393-B445 resembles the species described in Section II of the genus Flavobacterium which, however, involves heterogeneous species. Several investigators have recommended rearrangements of Flavobacterium species and proposed that gram-negative, non-motile, non-gliding, non-spreading strains with low GC content (≦40%) are to belong to the genus Flavobacterium, while gram-negative, non-motile or motile, peritrichous species with high GC content (60–70%) are to be transferred to the genus Empedobacter. In view of the morphological and physiological characteristics of strain G393-B445 and the new taxonomic criteria described above, strain G393-B445 is considered to belong to the genus Empedobacter.

Strain G393-B445 is believed to be a new species of the genus Empedobacter for the following reasons:

1. Strain G393-B445 may be clearly differentiated from the six species of Flavobacterium described in *Bergey's Manual* in its physiological and biochemical properties.
2. Strain G393-B445 may be differentiated from *Flavobacterium antibioticum* IFO-13715, a producing organism of peptide antibiotic BA-843 (Japan Kokai No. 130,601/53; Farmdoc 92052A/51) in its non-motility, lack of growth at 37° C., negative hydrolysis of sucrose and other biochemical responses.
3. One of the common characteristics of known Empedobacter species is halotolerance (positive growth in 5% NaCl). Strain G393-B445 in contrast has a distinct halophobic property and grows only at 1% or less NaCl concentration.

As in the case with other organisms, the characteristics of strain G393-B445 are subject to variation. For example, artificial variants and mutants of the G393-B445 strain may be obtained by treatment with various known mutagens such as ultraviolet rays, X-rays, high frequency waves, radioactive rays and chemicals. All natural and artificial variants and mutants (hereinafter referred to as mutants) of Empedobacter sp. strain G393-B445 which produce the Bu-2517 antibiotic are intended to be included within the scope of the present invention.

ANTIBIOTIC PRODUCTION

Antibiotic Bu-2517 is produced by cultivating a Bu-2517-producing strain of Empedobacter sp., most preferably the strain Empedobacter sp. strain G393-B445 having the identifying characteristics of ATCC 31962, or a mutant thereof, under submerged aerobic conditions in an aqueous nutrient medium. The organism is grown in a nutrient medium containing an assimilable carbon source, for example an assimilable carbohydrate. Examples of suitable carbon sources include glucose, ribose, galactose, fructose, mannose, sucrose, lactose, soluble starch and glycerol. The nutrient medium should also contain an assimilable nitrogen source such as fish meal, soybean meal, corn steep liquor, peptones, meat extract, peanut flour, yeast extract or ammonium salts. Inorganic salts such as sodium chloride, potassium chloride, magnesium sulfate, calcium carbonate, phosphates, etc. are added if necessary. Trace elements such as copper, manganese, iron, zinc, etc. are added to the medium if desired or may be supplied as impurities of other constituents of the media. The incubation temperature may be any temperature at which a Bu-2517-producing strain is able to grow, e.g. 7° C. to 42° C., but it is preferable to conduct the fermentation at 25°–35° C., especially 27°–32° C. A neutral or near-neutral initial pH is preferably employed in the medium and production of antibiotic is generally carried out for a period of from about 2 to 7 days. Ordinarily, optimum production is achieved in about 2 to 3 days (in shake cultures). For preparation of relatively small amounts, shake flasks and surface culture can be employed, but for the preparation of larger amounts, submerged aerobic culture in sterile tanks is preferred. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium. Aeration in tanks and bottles may be provided by forcing sterile air through or onto the surface of the fermenting medium. Further agitation may be provided by a mechanical impeller. Antifoaming agents such as lard oil may also be added if needed.

The production of Bu-2517 in the fermentation medium may readily be followed during the course of fermentation by the paper disc-agar diffusion assay using *Bacillus subtilis* PCI 219 as the test organism.

ISOLATION AND PURIFICATION OF BU-2517

After optimum broth potency has been obtained, the harvested broth is acidified to a pH of about 3 and then stirred with a water-immiscible organic solvent such as n-butanol. The organic solvent layer which contains the antibiotic activity is then separated and evaporated to dryness in vacuo. The residue may then be dissolved in an appropriate organic solvent, e.g. methanol, and the solution diluted with an appropriate antisolvent, e.g. acetone, to precipitate the Bu-2517 antibiotic as a crude solid.

The Bu-2517 antibiotic obtained as described above may be purified by ion exchange chromatography with an anionic exchange resin such as DOWEX 1-X2. As an example, the crude Bu-2517 may be applied to a column of DOWEX 1-X2 ($CH_3COO^-$form) and then successively developed with water, 0.5M ammonium acetate and a 1:1 (v/v) mixture of 1.0M ammonium acetatemethanol. The purified Bu-2517 is eluted with the methanolic ammonium acetate solution and may be further purified by column chromatography over a nonionic macroreticular polymer resin such as DIAION HP-20.

CHARACTERIZATION OF BU-2517

Bu-2517 is isolated as a white amorphous solid in the above-described purification process. The antibiotic is soluble in water (solubility: $>10\%$) at neutral and alkaline pH's. Its aqueous solution forms a precipitate in the pH range of 2.4~4.2. Bu-2517 is soluble in methanol, ethanol, aqueous dioxane, dimethylformamide and dimethylsulfoxide. It is less soluble in n-propanol, n-butanol and dioxane and practically insoluble in other organic solvents. Bu-2517 shows a positive response to Sakaguchi reagent but is negative in ninhydrin and anthrone reactions. The following Rf values were obtained with Bu-2517 in the silica gel (KIESELGEL $60F_{254}$, MERCK) thin layer chromatography (TLC) systems shown below:

Rf 0.55 10% ammonium acetate:methanol (1:1 v/v)
Rf 0.23 n-propanol:$H_2O$:acetic acid (70:30:1 v/v).

An analytical preparation of Bu-2517 melts at 224°–227° C. with decomposition. It shows a molecular weight of 1270 by osmometry and analyzes as $C_{49}H_{79}N_{11}O_{19}.5H_2O$. Calc'd: C48.38, H7.38, N12.67. Found: C48.51, H6.90, N12.53. Bu-2517 is an amphoteric substance with pKa's of 3.0, 4.1 and $>11.0$ in water, showing a titration equivalent of 1250. It is optically active: $[\alpha]_D^{26}+9°$ (c 1.0, $CH_3OH$). Bu-2517 exhibits no absorption maximum above 210 nm in the UV spectrum. The infrared spectrum of Bu-2517 shows a polyhydroxyl absorption at around 3350 $cm^{-1}$, an ester carbonyl at 1735 $cm^{-1}$ and amide carbonyl bands at 1630 and 1540 $cm^{-1}$. The proton NMR spectrum of Bu-2517 indicates the presence of a triplet methyl group and several methylene and methine protons. Aromatic or double bond protons are not observed.

STRUCTURE OF BU-2517

Bu-2517 was hydrolyzed with 6N HCl in a sealed tube at 105° C. for 16 hours. The resultant solution was shaken with diethyl ether to extract an acidic lipophilic substance. The aqueous layer containing a mixture of amino acid fragments was chromatographed on a column of DOWEX 50W-X4 to separate five amino acids-serine, proline, arginine and two unusual amino acids designated I and II. The structure of amino acid I was determined to be threo-$\beta$-hydroxyaspartic acid which has been reported as a microbiological metabolite produced by *Arthrinium phaeospermum* and Streptomyces sp. (*J. Antibiotics* 28:821–823, 1975). Amino acid II was identified as trans-L-3-hydroxyproline which has been known as one of the structural constituents of telomycin (*J. Am. Chem. Soc.* 85:2867–2868, 1963 and *Antibiotics Ann.* 1957/1958, 852–855).

The following molar ratio and chirality of the amino acid components of Bu-2517 were established as the result of quantitative amino acid analysis and the measurement of the optical rotation value for each of the amino acids isolated.

| Amino Acid | Molar Ratio | Chirality |
|---|---|---|
| threo-β-hydroxyaspartic acid | 2 | 1D + 1L |
| trans-3-hydroxyproline | 1 | 1L |
| serine | 2 | 2D |
| proline | 2 | 1D + 1L |
| arginine | 1 | 1L |

The acidic lipophilic substance extracted from the acid hydrolyzate of Bu-2517 was converted to its methyl ester and analyzed by NMR and mass spectrometry. The structure of the acidic compound was determined as 3-hydroxytetradecanoic acid having the formula $$CH_3-(CH_2)_{10}-\underset{OH}{\underset{|}{CH}}-CH_2-COOH.$$

As described above, three amino acid moieties having a β-hydroxy group are present as the structural constituents of Bu-2517. The amide linkage involving a β-hydroxyamino acid is known to be susceptible to acid hydrolysis through an N→O acyl migration. Thus, a controlled hydrolysis of Bu-2517 under mild acidic conditions afforded a series of small peptide fragments. Elucidation of the amino acid sequence for each of the peptide fragments by conventional methods established the total structure of Bu-2517 as shown below:

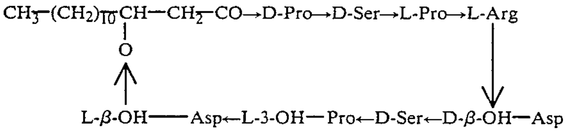

Pro = proline
Ser = serine
Arg = arginine
β-OH-Asp = threo-β-hydroxyaspartic acid
3-OH-Pro = trans-3-hydroxyproline

SALT FORMATION

As indicated above Bu-2517 is an amphoteric substance and forms salts with both acids and bases. Salts of Bu-2517 with pharmaceutically acceptable acids and bases are intended to be included within the scope of the present invention since they are substantially equivalent in antibiotic properties to Bu-2517 in its zwitterionic form. Suitable salts may be formed by conventional salt-forming procedures with organic or inorganic acids, metals (e.g. alkaline earth metals, alkali metals, aluminum, etc.), ammonia and organic bases. Examples of suitable salts include metal salts with sodium, potassium, calcium, magnesium and aluminum, ammonium salts, salts with amines such as triethylamine, n-propylamine, tri-n-butylamine, piperidine, ethanolamine, diethanolamine, triethanolamine, ethylenediamine, N,N'-dibenzylethylenediamine, benzylamine, tris(hydroxymethyl)aminomethane and pyrrolidine and salts with organic or inorganic acids such as hydrochloric, hydrobromic, sulfuric, phosphoric, acetic, propionic, oleic, palmitic, citric, succinic, nitric, lactic, tartaric, maleic, and the like. As an example of salt formation, Bu-2517 may be dissolved in water and suitable acid added to give an acid pH whereupon the solution may be lyophilized to give the desired acid addition salt. Similarly, base addition salts may be prepared by adding sufficient base to any aqueous solution of Bu-2517 to give a basic pH and then lyophilizing to recover the salt in solid form.

BIOLOGICAL PROPERTIES

Bu-2517 inhibits the growth of a variety of aerobic and anaerobic gram-positive bacteria both in vitro and in vivo.

The minimum inhibitory concentration (MIC) of Bu-2517 was determined for a variety of aerobic and anaerobic bacteria by the serial two-fold dilution method using a multi-inoculating apparatus. Mueller-Hinton agar was generally used for aerobic bacteria, GC medium (Eiken) for fastidious aerobic organisms such as streptococci, Neisseria and Haemophilus species, and GAM agar medium (a trademark of Nissui Co., Tokyo, Japan for an agar medium comprising peptone, protease peptone, yeast extract, liver extract, $KH_2PO_4$, soluble starch, sodium thioglycolate, agar, soybean peptone, digested blood powder, meat extract, glucose, NaCl and L-cysteine HCl) for anaerobic bacteria. The inoculum size was adjusted to $10^6$ CFU/ml for streptococci, Neisseria and Haemophilus species, $10^4$ for other aerobic bacteria and $10^7 \sim 10^8$ for all anaerobic organisms. Amphomycin, ampicillin, chloramphenicol, clindamycin, erythromycin, kanamycin and vancomycin were used as reference antibiotics.

The in vitro antibacterial spectrum of Bu-2517 for aerobic bacteria is shown in Table 4 below and for anaerobic organisms in Table 5. All of the aerobic gram-positive bacteria tested, which included many antibiotic-resistant staphylococci, were inhibited by Bu-2517 at 1.6 mcg/ml or less. Bu-2517 was generally 2~4 fold more active than amphomycin, an amphoteric peptide antibiotic, against staphylococci and 8~32 fold more active against streptococci. Bu-2517 showed no activity against aerobic gram-negative organisms. Against anaerobic bacteria, Bu-2517 inhibited all of the gram-positive rods and cocci tested, which included various species of Clostridium and Peptostreptococcus and strains of *Propionibacterium acnes.* Clindamycin-erythromycin-resistant strains of *C. difficile* and *C. perfringens* were susceptible to 1.6~3.1 mcg/ml of Bu-2517. Anaerobic gram-negative rod bacteria, such as Bacteroides and Fusobacterium species, were generally resistance to Bu-2517, while two strains of Veillonella species, gram-negative cocci, were inhibited at low concentration of Bu-2517. The antianaerobic activity of Bu-2517 was 2~16 times more potent than amphomycin.

TABLE 4

| | In Vitro Activity Against Aerobic Bacteria | | | | | | |
|---|---|---|---|---|---|---|---|
| | Bu-2517 | Amphomycin | Ampicillin | Chloramphenicol | Erythromycin | Kanamycin A | Vancomycin |
| Gram-positive bacteria | | | | | | | |
| *Staphylococcus aureus* 209P | 1.6 | 3.1 | 0.013 | 3.1 | 0.1 | 0.4 | 0.4 |
| *Staphylococcus aureus* Smith | 1.6 | 3.1 | 0.05 | 3.1 | 0.2 | 0.4 | 0.8 |

TABLE 4-continued

In Vitro Activity Against Aerobic Bacteria

| | Bu-2517 | Amphomycin | Ampicillin | Chloramphenicol | Erythromycin | Kanamycin A | Vancomycin |
|---|---|---|---|---|---|---|---|
| *Staphylococcus aureus* #193 | 1.6 | 3.1 | 1.6 | 3.1 | 0.4 | 0.8 | 0.8 |
| *Staphylococcus aureus* BX-1633 | 1.6 | 3.1 | 3.1 | 6.3 | 0.2 | 0.8 | 0.8 |
| *Staphylococcus aureus* A9601 | 1.6 | 3.1 | 0.4 | 6.3 | 0.4 | 0.4 | 0.8 |
| *Staphylococcus aureus* A9748 | 1.6 | 6.3 | 25 | 6.3 | 0.4 | 1.6 | 0.8 |
| *Staphylococcus aureus* A9856 | 0.8 | 3.1 | 0.05 | 3.1 | 0.2 | 0.8 | 0.8 |
| *Staphylococcus aureus* A20239 | 1.6 | 6.3 | 1.6 | 6.3 | 12.5 | >100 | 1.6 |
| *Staphylococcus aureus* A20394 | 1.6 | 3.1 | 3.1 | 50 | 0.2 | 0.8 | 0.4 |
| *Staphylococcus aureus* A20610 | 1.6 | 3.1 | 12.5 | 50 | >100 | 100 | 0.8 |
| *Staphylococcus aureus* A20701 | 1.6 | 6.3 | 25 | 50 | >100 | 100 | 0.8 |
| *Staphylococcus aureus* A22421 | 0.8 | 3.1 | 12.5 | 6.3 | 6.3 | >100 | 0.8 |
| *Streptococcus pyogenes* S-23 | 1.6 | 12.5 | 0.013 | | | | 0.8 |
| *Streptococcus pyogenes* Dick | 1.6 | 12.5 | 0.013 | | | | 0.8 |
| *Streptococcus pyogenes* A9604 | 1.6 | 12.5 | 0.013 | | | | 0.4 |
| *Streptococcus pneumoniae* IID-Type-I | 0.8 | 25 | 0.025 | | | | 0.8 |
| *Streptococcus pneumoniae* A9585 IID-Type-I | 1.6 | 25 | 0.025 | | | | 0.4 |
| *Streptococcus pneumoniae* A15069 IID-Type-I | 1.6 | 25 | 0.025 | | | | 0.4 |
| *Sarcina lutea* PCI-1001 | <0.05 | 0.8 | <0.05 | 1.6 | <0.05 | 3.1 | 0.4 |
| *Micrococcus flavus* D-12 | <0.05 | 0.4 | 0.1 | 1.6 | <0.05 | 3.1 | 0.2 |
| *Bacillus anthracis* IID-115 | 0.8 | 0.8 | 0.013 | 3.1 | 0.4 | 0.4 | 1.6 |
| *Bacillus subtilis* ATCC 6633 | 0.8 | 1.6 | 0.013 | 3.1 | <0.05 | 0.2 | 0.1 |
| Gram-negative bacteria | | | | | | | |
| *Escherichia coli* NIHJ | >100 | >100 | 0.4 | 0.8 | 100 | 0.8 | >100 |
| *Klebsiella pneumoniae* D-11 | >100 | >100 | 0.8 | 1.6 | 100 | 0.2 | >100 |
| *Proteus mirabilis* A9554 | >100 | >100 | 0.8 | 12.5 | >100 | 0.4 | >100 |
| *Proteus vulgaris* A9436 | >100 | >100 | 0.4 | 3.1 | 100 | 0.4 | >100 |
| *Pseudomonas aeruginosa* D-113 | >100 | >100 | >100 | >100 | 100 | >100 | >100 |
| *Neisseria gonorrhoeae* A15112 | >100 | >100 | 0.4 | | | | >100 |
| *Neisseria meningitidis* A20048 | >100 | >100 | 0.4 | | | | >100 |
| *Haemophilus influenzae* A9729 | >100 | >100 | 0.8 | | | | >100 |
| *Haemophilus influenzae* A22481 | >100 | >100 | 50 | | | | >100 |

TABLE 5

In Vitro Activity Against Anaerobic Bacteria

| | Bu-2517 | Amphomycin | Ampicillin | Chloramphenicol | Clindamycin | Erythromycin | Vancomycin |
|---|---|---|---|---|---|---|---|
| Gram-positive bacteria | | | | | | | |
| *Clostridium acidiurici* A9560 | 1.6 | 3.1 | 0.8 | 6.3 | 0.8 | 1.6 | 0.8 |
| *Clostridium chauvoei* A9561 | 3.1 | 6.3 | 0.4 | 6.3 | 0.025 | 1.6 | 0.8 |
| *Clostridium cylindrosporum* A9562 | 1.6 | 25 | 0.8 | 6.3 | 0.8 | 3.1 | 0.8 |
| *Clostridium difficile* A21675 | 1.6 | 3.1 | 1.6 | 3.1 | 100 | >100 | 0.8 |
| *Clostridium difficile* A21972 | 1.6 | 25 | 0.2 | 3.1 | 0.025 | 3.1 | 1.6 |
| *Clostridium perfringens* A9635 | 1.6 | 6.3 | 0.2 | 3.1 | 0.025 | 0.8 | 1.6 |
| *Clostridium perfringens* A22787 | 3.1 | 12.5 | 0.1 | 6.3 | 50 | >100 | 0.8 |
| *Clostridium ramosum* A21970 | 1.6 | 25 | 0.8 | 6.3 | 0.025 | 0.1 | >100 |
| *Clostridium septicum* A21869 | 1.6 | 6.3 | 0.8 | 6.3 | 0.8 | 0.8 | 0.8 |
| *Propionibacterium acnes* A21933 | 1.6 | 3.1 | 0.2 | 3.1 | 0.8 | 1.6 | 0.8 |
| *Propionibacterium acnes* A21953 | 6.3 | 6.3 | <0.0063 | 1.6 | 0.8 | 0.8 | 0.8 |
| *Propionibacterium acnes* A22650 | 0.8 | 6.3 | 0.05 | 0.4 | 0.1 | <0.0063 | 0.8 |
| *Peptostreptococcus anaerobius* A21905 | 0.8 | 3.1 | 0.1 | 1.6 | 0.2 | 0.8 | 0.4 |
| *Peptostreptococcus intermedius* A21881 | 3.1 | 6.3 | 0.1 | 3.1 | 0.2 | 0.4 | 1.6 |
| *Peptococcus magnas* A21676 | 1.6 | 6.3 | 0.1 | 1.6 | 0.05 | 0.8 | <0.05 |
| Gram-negative bacteria | | | | | | | |
| *Bacteroides fragilis* CUH-9 | 100 | >100 | 3.1 | 1.6 | 50 | 6.3 | 50 |
| *Bacteroides fragilis* CUH-24 | >100 | >100 | 50 | 1.6 | >100 | >100 | 25 |
| *Bacteroides fragilis* A20926 | 25 | 50 | 0.2 | 3.1 | 0.025 | <0.05 | 3.1 |
| *Bacteroides fragilis* A20928-1 | 25 | 25 | 0.2 | 3.1 | 0.025 | 0.013 | 3.1 |
| *Bacteroides fragilis* A20929 | 3.1 | 50 | 0.8 | 3.1 | 3.1 | 1.6 | 0.8 |
| *Bacteroides fragilis* A21900 | 6.3 | 25 | 0.2 | 3.1 | 1.6 | 0.4 | 6.3 |
| *Bacteroides fragilis* A22053 | >100 | >100 | 6.3 | 3.1 | 0.2 | 3.1 | 50 |
| *Bacteroides fragilis* A22533 | >100 | >100 | >100 | 3.1 | 0.025 | 0.4 | 50 |
| *Bacteroides fragilis* A22695 | >100 | >100 | >100 | 3.1 | 0.1 | 3.1 | 25 |
| *Bacteroides ovatus* A22400 | >100 | >100 | 25 | 1.6 | 6.3 | >100 | 50 |
| *Fusobacterium necrophorum* | >100 | >100 | >100 | 6.3 | 12.5 | >100 | >100 |

TABLE 5-continued

| | In Vitro Activity Against Anaerobic Bacteria | | | | | | |
|---|---|---|---|---|---|---|---|
| | Bu-2517 | Amphomycin | Ampicillin | Chloramphenicol | Clindamycin | Erythromycin | Vancomycin |
| A20013 | | | | | | | |
| *Fusobacterium nucleatum* A21906 | 12.5 | 6.3 | 12.5 | 6.3 | 1.6 | 1.6 | 0.8 |
| *Fusobacterium varium* ATCC 8501 | 50 | 25 | 12.5 | 6.3 | 1.6 | 1.6 | 6.3 |
| *Veillonella alcalescens* A21914-1 | 1.6 | 25 | 0.025 | 1.6 | 0.013 | 0.2 | 1.6 |
| *Venillonella parvula* A20010 | 1.6 | 6.3 | 0.4 | 3.1 | 0.4 | 3.1 | 0.8 |

The effectiveness of Bu-2517 in vivo was assessed in experimental infections of mice produced by the aerobic and anaerobic gram-positive pathogens, *S. aureus* Smith, *S. aureus* BX-1633, *S. pyogenes* A20201, *S. pneumoniae* A20759 and *C. perfringens.* Mice were challenged with a multiple of the lethal dose of the pathogens in a 5% suspension of hog gastric mucin (American Laboratory, Omaha, Neb.). Bu-2517 was administered intramuscularly just before the bacterial challenge. The mice were observed for 5 days to determine the median protective dose ($PD_{50}$). Amphomycin was comparatively tested as a reference antibiotic. As shown below in Table 6, the in vivo activity of Bu-2517 ranged from equal to up to three times the potency of amphomycin.

TABLE 6

| | | In Vivo Activity | | | |
|---|---|---|---|---|---|
| | Exp. | | | $PD_{50}$ (mg/kg, im) | |
| Challenge | Run | Challenge dose | | | Ampho- |
| organism | No. | cell/mouse | x $LD_{50}$ | Bu-2517 | mycin |
| *S. aureus* Smith | C-1247 | $1.3 \times 10^6$ | 350 | 3.3 | 9.0 |
| *S. aureus* Smith | C-1312 | $1.3 \times 10^6$ | 200 | 3.3 | 3.3 |
| *S. aureus* BX-1633 | C-1319 | $1 \times 10^7$ | 56 | 3.6 | 4.4 |
| *S. pyogenes* A20201 | C-1174 | $1.3 \times 10^2$ | 30 | 1.0 | — |
| *S. pyogenes* A20201 | C-1313 | $1.3 \times 10^2$ | 60 | 1.5 | 3.5 |
| *S. pneumoniae* A20759 | C-1176 | $6.3 \times 10^7$ | 20 | 1.9 | — |
| *C. perfringens* A9635 | C-1175 | $2.5 \times 10^7$ | 18 | 5.5 | — |
| *C. perfringens* A9635 | C-1318 | $2.5 \times 10^7$ | 11 | 6.8 | 7.4 |

Blood levels in mice were determined following an intravenous or intramuscular administration of Bu-2517. Blood samples were collected from orbital sinuses and assayed by the paper disc-agar diffusion method using *S. lutea* PCI 1001 as the test organism. As shown in Table 7, Bu-2517 was well absorbed parenterally and gave high and sustained blood levels. Upon an intramuscular administration of 30 mg/kg, a measurable blood level was still observed after 7 hours. Bu-2517 was not absorbed when administered orally.

TABLE 7

| | Blood Levels in Mice | | | | |
|---|---|---|---|---|---|
| Time after | Blood levels (mcg/ml) | | | | |
| admini- | intravenous dose | | intramuscular dose | | |
| stration | 10 mg/kg | 30 mg/kg | 10 mg/kg | 30 mg/kg | 100 mg/kg |
| 1 min | 70 | 224 | — | — | — |
| 5 | 41 | 162 | — | — | — |
| 10 | 33 | 131 | 11 | 22 | — |
| 15 | — | — | — | — | 45 |
| 20 | 23 | 68 | 13 | 32 | — |

TABLE 7-continued

| | Blood Levels in Mice | | | | |
|---|---|---|---|---|---|
| Time after | Blood levels (mcg/ml) | | | | |
| admini- | intravenous dose | | intramuscular dose | | |
| stration | 10 mg/kg | 30 mg/kg | 10 mg/kg | 30 mg/kg | 100 mg/kg |
| 30 | 18 | 73 | 14 | 48 | 45 |
| 45 | 18 | 64 | 14 | 41 | — |
| 1 hr | 14 | 50 | 13 | 36 | 47 |
| 1.5 | 7.9 | 32 | 11 | 35 | — |
| 2 | 5.6 | 23 | 8.9 | 28 | — |
| 3 | 3.1 | 14 | 5.3 | 18 | 55 |
| 5 | — | — | <2.0 | 8.9 | — |
| 7 | — | — | — | 3.8 | 23 |
| 10 | — | — | — | — | 15 |
| 24 | — | — | — | — | <0.3 |
| Half life (hr.) | 0.81 | 0.87 | 1.6 | 1.8 | 3.7 |
| AUC* (mcg · hr/ml) | 39 | 163 | 40 | 137 | 460 |

*area under curve

The acute toxicity of Bu-2517 was determined by intravenous and intramuscular routes. No death occurred up to a dose of 400 mg/kg (iv) or 1600 mg/kg (im). Mice died with an intravenous dose at 800 mg/kg, the intravenous $LD_{50}$ being calculated as 560 mg/kg.

As indicated by the in vitro and in vivo data discussed above, Bu-2517 is useful as an antibacterial agent which can be used alone or in combination with other antibacterial agents to prevent the growth of, or reduce the number of, gram-positive aerobic and anaerobic bacteria. It is especially useful as a therapeutic agent in poultry and animals, including man, for the treatment of infectious diseases caused by bacteria sensitive to Bu-2517. Also, Bu-2517 is valuable as a nutritional supplement in animal feeds and as an agent for the treatment of acne.

The present invention includes within its scope pharmaceutical compositions containing an effective antibacterial amount of Bu-2517 (including pharmaceutically acceptable salts thereof) in combination with an inert pharmaceutically acceptable carrier or diluent. Such compositions may be made up in any pharmaceutical form appropriate for the route of administration in question. Examples of such compositions for parenteral administration include sterile solutions, suspensions and emulsions. Parenteral dosage forms can also be manufactured in the form of sterile solid compositions which can be dissolved in sterile water, physiological saline or some other sterile injectable medium immediately before use. Bu-2517 can also be incorporated into topical preparations such as ointments, creams, lotions, emulsions, salves, emollients and sprays.

The Bu-2517 antibiotic of the present invention (including pharmaceutically acceptable salts thereof) is administered so that the concentration of antibiotic is greater than the minimum inhibitory concentration for the particular organism being treated. It will of course be appreciated that the actual dose of antibiotic used will be determined by the physician or veterinarian after consideration of such factors as age, body weight, sex, diet, route of administration, rate of excretion, condition of the patient, drug combinations and the particular situs and disease being treated.

The present invention also provides a method for therapeutically treating an animal host (particularly poultry and mammals including man) affected by a gram-positive aerobic or anaerobic bacteria which comprises administering to said host an effective antibacterial dose of Bu-2517 or a pharmaceutically acceptable salt thereof.

The following examples are provided for illustrative purposes only and are not intended to limit the scope of the invention. DIAION HP-20 (trademark of Mitsubishi Chemical Industries, Japan) is a nonionic macroreticular (macroporous) polymer resin. DOWEX 1-X2 (trademark of Dow Chemical Co., Midland, Mich., USA) is a strongly basic anion exchange resin of the polystyrene type. DOWEX 50W-X4 (trademark of Dow Chemical Co.) is a strongly acidic cation exchange resin of the polystyrene type.

EXAMPLE 1

Fermentation of Bu-2517

A well-grown agar slant of a biologically pure culture of Empedobacter sp. strain G393-B445 was used to inoculate seed medium containing 2% soluble starch, 1% glucose, 0.2% meat extract, 0.2% yeast extract, 0.5% NZ Case (a trademark of Sheffield Products, Norwich, N.Y., U.S.A. for a tryptic digest of casein) and 0.2% $CaCO_3$, the pH being adjusted to 7.0 before sterilization. The seed culture was incubated at 28° C. for 24 hours on a rotary shaker (250 rpm), and 5 ml of the growth was transferred to a 500 ml Erlenmeyer flask containing 100 ml of fermentation medium composed of 3% sucrose, 2% linseed meal, 0.3% $(NH_4)_2SO_4$ and 0.5% $CaCO_3$. The pH of the medium was adjusted to 7.0 before sterilization. The fermentation was carried out on a rotary shaker at 28° C. and the antibiotic activity in the fermentation broth followed by a paper disc-agar diffusion assay using *Bacillus subtilis* PCI 219 as the test organism. The antibiotic production in shake cultures generally reached a maximum after 48∼70 hours.

Fermentation studies were also performed in 20 liter jar fermentors which contained 10 liters of the production medium having the same composition as described above. The fermentors were operated at 28° C. with stirring at 250 rpm for 20∼23 hours.

EXAMPLE 2

Recovery of the Bu-2517 Antibiotic

The harvested broth of Bu-2517 (37 L) was acidified to pH 3.0 with an addition of 6N HCl and stirred with an equal volume of n-butanol for 1 hour. The n-butanol layer which contained the antibiotic activity was separated and evaporated in vacuo until dryness. The residue was dissolved in methanol (100 ml) and the solution diluted with 1 L of acetone to precipitate a crude solid of the Bu-2517 antibiotic (21 g). This solid was applied on a column of DOWEX 1-X2 ($CH_3COO^-$form, 800 ml) which was successively developed with water (5 L), 0.5M ammonium acetate (5 L) and a 1:1 (v/v) mixture of 1.0M ammonium acetate:methanol (5 L). The bioactive fractions eluted with the methanolic ammonium acetate solution were pooled and concentrated in vacuo to a small volume (ca. 80 ml). The solution was passed through a column of DIAION HP-20 (800 ml) which was developed with water (6 L), 50% aqueous methanol (3 L) and 80% aqueous methanol (5 L), successively. Evaporation in vacuo of bioactive fractions obtained from the 80% aqueous methanol eluate afforded a pure preparation of Bu-2517 (3.80 g) as a white solid.

We claim:

1. A process for producing the peptide antibiotic Bu-2517 which comprises cultivating Empedobacter sp. ATCC 31962 or a Bu-2517-producing mutant thereof under submerged aerobic conditions in an aqueous nutrient medium containing assimilable sources of carbon and nitrogen until a substantial amount of Bu-2517 is produced by said organism in said culture medium and then recovering the Bu-2517 antibiotic from the culture medium.

2. The process according to claim 1 wherein the Bu-2517-producing strain is Empedobacter sp. ATCC 31962.

3. The process according to claim 3 or claim 2 which includes the additional step of converting the Bu-2517 antibiotic into a pharmaceutically acceptable salt thereof.

4. A biologically pure culture of the microorganism Empedobacter sp. strain G393-B445 (ATCC 31962), said culture being capable of producing the antibiotic Bu-2517 of the formula

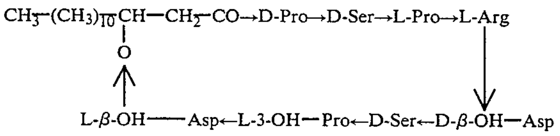

wherein Pro represents proline, Ser represents serine, Arg represents arginine, β-OH-Asp represents threo-β-hydroxyaspartic acid and 3-OH-Pro represents trans-3-hydroxyproline in a recoverable quantity upon cultivation in an aqueous nutrient medium.

* * * * *